United States Patent [19]

Billman et al.

[11] 4,026,915
[45] May 31, 1977

[54] DI-MIXED ALKY ASPARTATE SALTS

[75] Inventors: Fred L. Billman; Hung-Hee H. Lee, both of Racine, Wis.

[73] Assignee: S. C. Johnson & Son, Inc., Racine, Wis.

[22] Filed: Aug. 27, 1975

[21] Appl. No.: 608,376

[52] U.S. Cl. .............................. 260/471 A; 252/8.8; 260/247.1 E; 260/247.2 R; 260/247.2 A; 260/247.2 B

[51] Int. Cl.² .............. C07C 103/54; C07C 103/48

[58] Field of Search ......... 260/247.2, 482 P, 247.1, 260/471 A

[56] References Cited
FOREIGN PATENTS OR APPLICATIONS 7,311,206   2/1976   Netherlands

*Primary Examiner*—Henry R. Jiles
*Assistant Examiner*—R. W. Ramsuer

[57] ABSTRACT

Novel fabric softener compounds having the formula

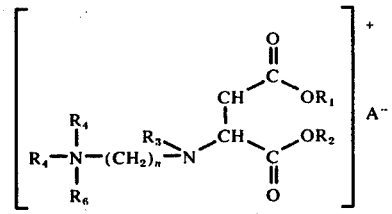

wherein R is hydrogen or methyl, $R_1$ and $R_2$ are the same or different and are selected from linear and branched chain alkyl groups having from 8 to 22 carbon atoms; $R_3$ is selected from hydrogen, formyl, acetyl, benzoyl; $R_4$ and $R_5$ being the same or different and selected from lower alkyl groups having from 1 to 4 carbon atoms, -hydroxyalkyl groups having from 2 to 4 carbon atoms and $R_4$ and $R_5$ taken together are diethylene oxide, $R_6$ is selected from hydrogen, lower alkyl having from 1 to 4 carbon atoms and benzyl; $n$ is a whole number selected from 2 to 10; and A is an anion selected from methyl sulfate, ethyl sulfate, chlorides, fluorides, sulfates, acetates, bromides, iodides, benzoates and gluconates.

16 Claims, No Drawings

DI-MIXED ALKY ASPARTATE SALTS

This invention relates to novel fabric softening compounds. More particularly, this invention relates to novel fabric softening compounds which are produced from the reaction of maleic, fumaric, citraconic and mesaconic acid esters and various alkyl diamines.

In general, fabric softening compositions are cationic or cationic-amphoteric surface active agents, such as the di-lower alkyl, di-long chain fatty ammonium quaternary compounds and the imidazoline type quaternary compounds. These materials, although quite effective in softening fabrics in the rinse cycle and occasionally in the wash cycle, depend heavily upon tallow and other animal by-products for their formation and accordingly are subject to wide variations in availability, cost, quality and other factors.

Cationic fabric softeners function by depositing their positive particles onto a negatively charged surface, such as laundry, so as to render the same softer and more pleasing to the touch. The conventional form of addition of these softeners is in the rinse cycle subsequent to the complete removal of the detergent since many detergents utilized are of the anionic type which tend to deactivate or neutralize these cationically charged materials.

Since the materials presently available are generally formed from natural sources, many of these compounds have various malodors which are the result of amine functionality or the various natural materials utilized as starting material, such as tallow and other ingredients. In view of the odors which are often deposited on the clothing by these compounds, various formulators have developed perfumes which tend to mask or inhibit these odors.

It has now been found that the novel fabric softeners of the present invention are suitable and active rinse cycle fabric softeners and some of the compounds of the present invention are also applicable as wash cycle softeners for use with anionic, cationic and nonionic detergents. Lastly, some of the softener compounds of the present invention also have substantially no malodor commonly associated with cationic fabric softening compounds.

Accordingly, it is the object of the present invention to provide a novel class of compounds formed by the reaction of alkyl diamines with maleic, fumaric, mesaconic and citraconic esters to produce fabric softening compositions. It is a further object of the present invention to provide fabric softening compounds which have a high degree of activity requiring a relatively low solids level to produce effective softening.

It is a still further object of the present invention to provide fabric softening compounds which also function as wash cycle softeners in the presence of anionic detergents.

It is a still further object of the present invention to provide fabric softening compounds which have substantially no malodor commonly associated with fabric softening materials.

Still further objects and advantages of the compounds of the present invention will become more apparent from the following, more detailed description thereof.

Compounds of the present invention can be generally represented by the following formula:

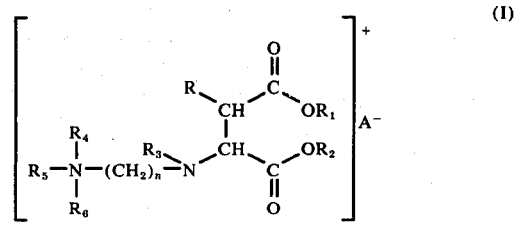

wherein R is hydrogen and methyl, $R_1$ and $R_2$ are the same or different and are selected from linear or branched alkyl groups having from 8 to 22 carbon atoms and mixtures thereof; $R_3$ is selected from hydrogen, formyl, acetyl and benzoyl; $R_4$ and $R_5$ are selected from lower alkyl having from 1 to 4 carbon atoms, ω-hydroxyalkyl having from 2 to 4 carbon atoms and $R_4$ and $R_5$ taken together are diethylene oxide; $R_6$ is selected from hydrogen, lower alkyl having from 1 to 4 carbon atoms and benzyl; $n$ is an integer from 2 to 10; and A is an anion.

The anhydrides suitable for forming the compounds of the present invention are maleic anhydride, fumaric anhydride, mesaconic anhydride, citraconic anhydride and mixtures. Preferred anhydrides are maleic and fumaric anhydride.

The ester substituent in the compounds of the present invention is selected from linear or branched chain alkyl groups having 8 to 22 carbon atoms and preferably from 14 to 22 carbon atoms. These alkyl groups can be derived from pure alcohols or from mixtures of long chain alcohols. Natural higher alkyl alcohols contain a mixture of chain lengths and even numbers of carbon atoms groups predominate. Examples of some higher alcohols are octanol, nonanol, decanol, dodecanol, tetradecanol, hexadecanol, octadecanol, eicosanol, docosanol and the like. Also, some commercially available mixed alcohols are useful, such as the Alfols from Conoco Chemical. Alternatively, the esters can be formed from the reaction of the corresponding acids and a long-chain C18-C22 α-olefin such as 1-octene, 1-nonene, 1-decene, 1-dodecene, 1-tetradecene, 1-hexadecene, 1-octadecene, 1-eicosene, 1-docosene and the like. Mixed α-olefins are also suitable starting materials.

The compositions of the present invention may have a variety of substituents for $R_3$, $R_4$, $R_5$, $R_6$ and A. In general, $R_3$ is selected from hydrogen, formyl, acetyl and benzoyl with hydrogen, acetyl and formyl being preferred, hydrogen and acetyl being most preferred. Because of the method of preparation and the starting materials used, $R_4$ and $R_5$ will often be the same group, although this is not necessary for fabric softening effectiveness. Generally, $R_4$ and $R_5$ are selected from lower alkyl having 1 to 4 carbon atoms, i.e., methyl, ethyl, isopropyl, propyl, n-butyl and isobutyl, lower ω-hydroxyalkyl having 2 to 4 carbon atoms, i.e., 2-hydroxyethyl, 3-hydroxypropyl and 4-hydroxybutyl, and when $R_4$ and $R_5$ are taken together are diethyllene oxide. The preferred substituents for $R_4$ and $R_5$ are methyl, ethyl, 2-hydroxyethyl and diethylene oxide with methyl, 2-hydroxyethyl and $R_4$ and $R_5$ taken together are diethylene oxide being most preferred.

The $R_6$ and A substituents are the residue and anion from the quaternary cation or salt formation. $R_6$ is selected from lower alkyl having 1 to 4 carbon atoms, i.e., methyl, ethyl, propyl, isopropyl, butyl and isobutyl, hydrogen and benzyl with hydrogen, methyl, ethyl and benzyl being preferred. The most preferred are hydrogen and methyl. The anion A is selected from anions imparting water dispersability including lower alkyl sulfates such as methyl sufate and ethyl sulfate, halides such as fluoride, chloride, bromide and iodide, sulfates, carboxylates such as acetate, benzoate, formate and gluconate, with formate methyl sulfate, ethyl sulfate, gluconate and chloride being preferred. Most preferred are methyl sulfate and chloride.

$R_6$ and A are formed by reacting the non-ionized intermediate with organic or inorganic acids to form salts or quaternizing agents to form quaternary compounds.

The compounds of the present invention are readily prepared either by the reaction of the two moles of a higher alkyl alcohol or mixed higher alkyl alcohols, such as fatty alcohols, with one mole of maleic, fumaric, citraconic or mesaconic anhydride in the presence of an acid catalyst, such as p-toluene sulfonic acid and the like, in a benzene solvent, or the reaction of two moles of α-olefin with one mole of maleic or fumaric acid. The former reaction produces one mole of water and one mole of a mixture of maleic and fumaric acid diesters having the formula

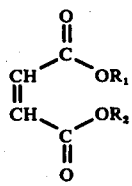

(II)

wherein $R_1$ and $R_2$ are the same or different. Since the reaction of alcohol and anhydride is sequential, one mole of an alcohol can be reacted with the anhydride followed by the reaction of the monoester with a second mole of a different alcohol.

This diester is then reacted with an alkyl diamine having 1 tertiary amine group and one primary or secondary amine group, and also having from 2 to 10 carbon atoms and preferably 3 carbon atoms, such as dimethyl propyl diamine, N-amino propyl morpholine, di(2-hydroxyethyl) propyl diamine and the like, at a temperature of from 80° to 110° C for from 2 to 3 hours. Generally, this reaction is on a one mole to one mole ratio; however, it is generally desirable to use a 10% excess of the diamine so as to force the reaction to completion to produce an intermediate having the formula

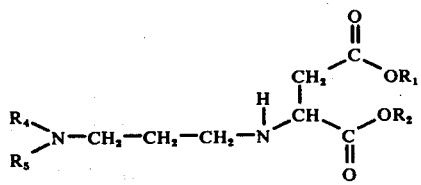

(III)

wherein $R_1$, $R_2$, $R_4$ and $R_5$ are as previously defined. Where $R_3$ is other than hydrogen, this intermediate is reacted with a suitable reagent such as formyl chloride, acetyl chloride or benzoyl chloride to form an intermediate as set forth in formula IV.

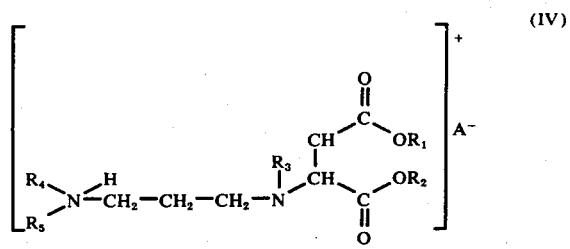

(IV)

Intermediate III is then reacted with an organic or inorganic acid, such as hydrochloric acid, benzoic acid, formic acid, acetic acid, sulfuric acid, gluconic acid and the like, or quaternizing agent, such as dimethyl sulfate, diethyl sulfate, methyl chloride, methyl bromide, methyl iodide and the like, to form the compound as set forth in formula I.

It is important to the stability of the resulting product that there be from 2 to 10 and preferably 3 carbons between the primary and tertiary nitrogens. These compounds are relatively stable and are easily produced in good yield by the reaction sequence set forth above.

The precise conditions employed in reacting of the various components to produce the compounds of the present invention will, of course, vary depending upon the nature of these materials with some of the components requiring shorter or longer reaction times so as to produce complete reactions.

Illustrative compounds within the scope of the present invention include the following compounds:
1. di-mixed C14-C18 alkyl N-formyl-N-[3-(dimethylamino) propyl] aspartate, N'-dimethyl sulfate quaternary
2. di-mixed C14-C18 alkyl-N-[3-(dimethylamino) propyl]aspartate, N'-acetic acid salt
3. di-mixed C14-C18 alkyl-N-[3-(dimethylamino) propyl] aspartate, N'-methyl iodide quaternary
4. di-mixed C14-C18 alkyl-N-[3-(dimethylamino) propyl] aspartate, N'-benzoic acid salt
5. di-mixed C14-C18 alkyl-N-[3-(dimethylamino) propyl] aspartate, N'-diethyl sulfate quaternary
6. di-mixed C14-C18 alkyl-N-[3-(dimethylamino) propyl] aspartate, N'-methyl bromide quaternary
7. di-mixed C14-C18 alkyl-N-[3-(dimethylamino) propyl] aspartate, N-methyl chloride quaternary
8. di-mixed C14-C18 alkyl-N-formyl N-[3-(dimethylamino) propyl] aspartate, N'-diethyl sulfate quaternary
9. di-mixed C14-C18 alkyl-N-formyl N-[3-(dimethylamino) propyl] aspartate, N'-methyl iodide quaternary
10. di-mixed C14-C18 alkyl-N-formyl N-[3-(dimethylamino) propyl] aspartate, N'-methyl bromide quaternary
11. di-mixed C14-C18 alkyl N-formyl-N-[3-(dimethylamino) propyl] aspartate, N'-methyl chloride quaternary
12. didodecyl-N-acetyl-N-[3-(dimethylamino) propyl] aspartate, N'-hydrochloride salt
13. dodecyl-octadecyl-N-acetyl-N-[3-(dimethylamino) propyl] aspartate, N'-hydrochloride salt
14. di-mixed C18-C22 alkyl-N-[3-di(2-hydroxyethyl) aminopropyl] aspartate, N'-hydrochloride salt
15. di-mixed C18-C22 alkyl-N-[3-(dimethylamino) propyl] aspartate, N'-dimethyl sulfate quaternary 16. di-mixed C18-C22 alkyl-N-[3-(dimethylamino) propyl] aspartate, N'-formic acid salt
17. di-mixed C18-C22 alkyl-N-acetyl-N-[3-(dimethylamino) propyl] aspartate, N'-hydrochloride salt
18. di-mixed C18-C22 alkyl-N-[3-(dimethylamino) propyl] aspartate, N'-gluconic acid salt
19. di-mixed C14-C18 alkyl-N-[3-(dimethylamino) propyl] aspartate N'-dimethyl sulfate quaternary
20. di-mixed C14-C18 alkyl-N-acetyl-N-[3-(dimethylamino) propyl] aspartate, N'-hydrochloride salt
21. di-mixed C14-C18 alkyl-N-[3-(dimethylamino) propyl] aspartate, N'-formic acid salt
22. di-mixed C14-C18 alkyl-N-formyl-N-formyll-N-[3-(dimethylamino) propyl] aspartate, N'-benzyl chloride quaternary
23. di-mixed C14-C18 alkyl-N-[3-(dimethylamino) propyl] aspartate N'-benzyl chloride quaternary
24. dioctadecyl-N-[3-(dimethylamino) propyl] aspartate, N'-dimethyl sulfate quaternary
25. di-mixed C18-C22 alkyl-N-[3-(dimethylamino) propyl] aspartate, N'-hydrochloride salt
26. di-mixed C14-C18 alkyl-N-[3-(4-morpholino) propyl] aspartate, N'-dimethyl sulfate quaternary
27. di-mixed C14-C18 alkyl-N-[3-(dimethylamino) propyl] aspartate, N'-sulfuric acid salt
28. di-mixed C14-C18 alkyl-N-benzoyl-N-[3-(dimethylamino) propyl] aspartate, N'-hydrochloride salt
29. didecyl-N-acetyl-N-[3-(dimethylamino) propyl] aspartate, N'-methyl chloride quaternary
30. di-mixed C14-C18 alkyl-N-[3-(dimethylamino) propyl] aspartate, N'-hydrochloride salt
31. dioctyl-N-acetyl-N-[3-(dimethylamino) propyl] aspartate, N'-hydrochloride salt
32. di-mixed C18-C22 alkyl-N-[3-di(2-hydroxyethyl) amino propyl] aspartate, N'-gluconic acid salt
33. di-mixed C18-C22 alkyl-N-[3-(dimethylamino) propyl]-2-methyl aspartate, N'-dimethyl sulfate quaternary.

Of course, the foregoing list of compounds is for the purpose of illustration only and should be in no way taken as limiting the scope of the subject matter of the present invention.

The compounds of the present application, as noted above, have particular utility with regard to the softening of fabrics in the rinse cycle. Although it is not possible to predict with certainty whether or not a given compound will have wash cycle effectiveness, it has been found that all the compounds within the scope of the present invention have some activity as rinse cycle softeners and that the following compounds have been found to be effective wash cycle softeners:

di-mixed C14-C18 alkyl-N-acetyl-N-[3-(dimethylamino) propyl] aspartate, N'-hydrochloride salt;
di-mixed C18-C22 alkyl-N-[3-(dimethylamino) propyl] aspartate, N'-hydrochloride salt;
di-mixed C14-C18 alkyl-N-[alkyl-N-3-(dimethylamino) propyl] aspartate, N'-formic acid salt;
di-mixed C14-C18 alkyl-N-formyl-N-[3-(dimethylamino) propyl] aspartate, N'-benzyl chloride quaternary;
di-mixed C14-C18 alkyl-N-[3-(dimethylamino) propyl] aspartate, N'-benzyl chloride quaternary;
di-mixed C14-C18 alkyl-N-[3-(4-morpholino) propyl] aspartate, N'-dimethyl sulfate quaternary;
di-mixed C18-C22 alkyl-N-acetyl-N-[3-(dimethylamino) propyl] aspartate, N'-hydrochloride salt; and
di-mixed C14-C18 alkyl-N-[3-(dimethylamino) propyl] aspartate, N'-dimethyl sulfate quaternary.

Preferred wash cycle softeners are:
di-mixed C18-C22 alkyl-N-[3-(dimethylamino) propyl] aspartate, N'-hydrochloride salt;
di-mixed C14-C18 alkyl-N-[3-(dimethylamino propyl] aspartate, N'-hydrochloride salt;
di-mixed C14-C18 alkyl-N-formyl-N-[3-(dimethylamino propyl] aspartate, N'-benzyl chloride quaternary;
di-mixed C18-C22 alkyl-N-[3-dimethylamino) propyl] aspartate, N'-hydrochloride salt;
di-mixed C14-C18 alkyl-N-[3-(4-morpholino) propyl] aspartate, N'-dimethyl sulfate quaternary; and
di-mixed C14-C18 alkyl-N-[3-(dimethylamino) propyl] aspartate, N'-formic acid salt.

Also, as noted above, many fabric softeners known in the art have an odor problem which must be masked or hidden by various expensive perfumes. It has been found that certain compounds within the scope of the present invention are not only effective softeners but also have substantially no malodor, therefore, do not require the utilization of large amounts of expensive masking perfumes:

di-mixed C14-C18 alkyl-N-[3-(dimethylamino) propyl] aspartate, N'-methyl iodide quaternary;
di-mixed C14-C18 alkyl-N-[3-(dimethylamino) propyl] aspartate, N'-benzoic acid salt;
di-mixed C14-C18 alkyl-N-[3-dimethylamino) propyl] aspartate, N'-diethyl sulfate quaternary;
di-mixed C14-C18 alkyl-N-formyl N-[3-(dimethylamino) propyl] aspartate, N'-diethyl sulfate quaternary;
di-mixed C18-C22 alkyl-N-[3-di(2-hydroxyethyl) aminopropyl] aspartate, N'-hydrochloride salt;
di-mixed C18-C22 alkyl-N-[3(dimethylamino) propyl] aspartate, N'-formic acid salt;
di-mixed C18-C22 alkyl-N-[3-dimethylamino) propyl] aspartate, N'-hydrochloride salt; di-mixed C18-C22 alkyl-N-[3-(dimethylamino) propyl] aspartate, N'-gluconic acid salt;
di-mixed C14-C18 alkyl-N-[3-(dimethylamino) propyl] aspartate, N'-dimethyl sulfate quaternary;
di-mixed C14-C18 alkyl-N-[3-(dimethylamino) propyl] aspartate, N'-formic acid salt;
di-mixed C14-C18 alkyl-N-formyl-N-[3-(dimethylamino) propyl] aspartate, N'-benzyl chloride quaternary;
di-mixed C14-C18 alkyl-N-[3-(dimethylamino) propyl] aspartate, N'-benzyl chloride quaternary;
di-mixed C18-C22 alkyl-N-[3-(dimethylamino) propyl] aspartate, N'-hydrochloride salt;
di-mixed C14-C18 alkyl-N-[3-(4-morpholino) propyl] aspartate, N'-dimethyl sulfate quaternary;
di-mixed C14-C18 alkyl-N-[3-(dimethylamino) propyl] aspartate, N'-sulfuric acid salt; and
di-mixed C14-C18 alkyl-N-benzoyl-N-[3-(dimethylamino) propyl] aspartate, N'-hydrochloride salt.

The compounds of the present invention are useful as wash and/or rinse cycle softeners. Although almost all of the compounds of the present invention have some rinse cycle softening activity, the following compounds show particularly high rinse cycle softening activity:
di-mixed C14-C18 alkyl N-formyl-N-[3-(dimethylamino) propyl] aspartate, N'-dimethyl sulfate quaternary;
di-mixed C14-C18 alkyl-N-[3-(dimethylamino) propyl] aspartate, N'-acetic acid salt;

di-mixed C14-C18 alkyl-N-[3-(dimethylamino) propyl] aspartate, N'-methyl iodide quaternary;
di-mixed C14-C18 alkyl-N-[3-(dimethylamino) propyl] aspartate, N'-benzoic acid salt;
di-mixed C14-C18 alkyl-N-[3-(dimethylamino) propyl] aspartate, N'-diethyl sulfate quaternary;
di-mixed C14-C18 alkyl-N-[3-(dimethylamino) propyl] aspartate N'-methyl chloride quaternary;
di-mixed C14-C18 -N-formyl N-[3-(dimethylamino propyl] aspartate, N'-diethyl sulfate quaternary;
di-mixed C14-C18 alkyl N-formyl-N-[3-(dimethylamino propyl] aspartate, N'-methyl chloride quaternary;
dodecyl-octadecyl-N-[3-(dimethylamino) propyl] aspartate, N'-hydrochloride salt;
di-mixed C18-C22 alkyl-N-[3-di(2-hydroxyethyl) aminopropyl] aspartate, N'-hydrochloride salt;
di-mixed C18-C22 alkyl-N-[3-(dimethylamino) propyl] aspartate, N'-dimethyl sulfate quaternary;
di-mixed C18-C22 alkyl-N-[3-(dimethylamino) propyl] aspartate, N'-formic acid salt;
di-mixed C18-C22 alkyl-N-acetyl-N-[3-(dimethylamino) propyl] aspartate, N'-hydrochloride salt;
di-mixed C18-C22 alkyl-N-[3-(dimethylamino) propyl] aspartate, N'-gluconic acid salt;
di-mixed C14-C18 alkyl-N-[3-(dimethylamino) propyl] aspartate, N'-dimethyl sulfate quaternary;
di-mixed C14-C18 alkyl-N-acetyl-N-[3-(dimethylamino) propyl] aspartate, N'-hydrochloride salt;
di-mixed C14-C18 alkyl-N-[3-(dimethylamino) propyl] aspartate, N'-formic acid salt;
di-mixed C14-C18 alkyl-N-formyl-N-[3-(dimethylamino) propyl] aspartate, N'-benzyl chloride quaternary;
di-mixed C18-C22 alkyl-N-[3-(dimethylamino) propyl] aspartate, N'-hydrochloride salt; and
di-mixed C14-C18 alkyl-N-[3-(dimethylamino) propyl] aspartate, N'-sulfuric acid salt.

The following compounds are most preferred for use as rinse cycle fabric softeners:
di-mixed C14-C18 alkyl-N-[3-(dimethylamino) propyl] aspartate, N'-methyl chloride quaternary;
di-mixed C14-C18 alkyl-N-formyl N-[3-(dimethylamino) propyl] aspartate, N'-diethyl sulfate quaternary;
di-mixed C18-C22 alkyl-N-[3-di(2-hydroxyethyl)aminopropyl] aspartate, N'-hydrochloride salt;
di-mixed C18-C22 alkyl-N-[3-(dimethylamino) propyl] aspartate, N'-dimethyl sulfate quaternary;
di-mixed C18-C22 alkyl-N-[3-(dimethylamino) propyl] aspartate, N'-formic acid salt;
di-mixed C18-C22 alkyl-N-acetyl-N-[3-(dimethylamino) propyl] aspartate, N'-hydrochloride salt; and
di-mixed C18-C22 alkyl-N-[3-(dimethylamino) propyl] aspartate, N'-gluconic acid salt.

In use, the compounds of the present application may be packaged in a suitable solvent so that the same may be easily mixed with the wash to rinse water as desired. It is preferable to produce the compounds of the present application in as concentrated a solution or dispersion as possible so as to allow the housewife to utilize a relatively small volume or amount of the material during each use.

The following representative examples are illustrative of the preparation of compounds of the present invention:

EXAMPLE 1

Preparation of di-mixed C18-C22 alkyl maleate 196.2 grams (2 moles) of maleic anhydride, 200 mole liters of dry benzene, 1,809.6 grams (4 moles) of Alfol C20+ (hydrocarbon mixture containing C18, C20, C22 alcohols and 30% paraffin, primarily C20 and C22 available from Conoco) and 8 grams of camphor sulfonic acid refluxed for 1 hour. 36 milliliters of water was azeotroped off over a 5-hour period and the temperature rose from 90° to 150° C. The solvent was then removed by vacuum distillation to yield 1,951 grams of product. The saponification number observed was 112 compared to the theoretical 113.9. IR spectrum analysis confirmed the structure.

EXAMPLE 2

Preparation of di-mixed C18-C22 alkyl-N-[3-(dimethylamino) propyl] aspartate

Some 930 grams (0.94 mole) of the product of Example 1 was melted at 95° C and 96.5 grams (0.94 mole) of N,N-dimethylpropylene diamine was added dropwise over the period of 1 hour with stirring. Stirring was continued at 100° to 105° C for 3 hours to yield a product of 1,029 grams. The theoretical saponification number was 113.9, while the observed saponification number was 112. The structure was confirmed by IR and NMR analysis. The resultant product was 87% cationic.

EXAMPLE 3

Preparation of di-mixed C18-C22 alkyl-N-[3-(dimethylamino) propyl] aspartate, N'-hydrochloride salt Some 150 grams (0.138 mole) of the product of Example 2 was dissolved in 50 milliliters of isopropyl alcohol at 45° C. This mixture was stirred while a solution of 11.5 milliliters (0.138 mole) of concentrated hydrochloric acid in 8.5 milliliters of water was added dropwise over a period of ½ hour. The mixture was stirred at 40° C for 2 hours and the solvent was removed by bubbling nitrogen into the 60° C mixture for 3 hours. The resultant product contained 20% isopropanol and weighed 197 grams. IR analysis confirmed the structure, and the product had 55% cationic, 0% quaternary and 0% free amine.

EXAMPLE 4

Preparation of di-mixed C18-C22 alkyl-N-[3-(dimethylamino) propyl] aspartate, N'-dimethylsulfate quaternary Some 150 grams of the product of Example 2 was dissolved in 50 milliliters of isopropanol at 50° C followed by heating to 75° C. At this time, 17.41 grams (0.138 mole) of dimethyl sulfate was added dropwise over a period of 1 hour, producing an exothermic reaction raising the temperature from 75° to 100° C. After 2 hours of stirring at 100° to 105° C, the solvent was removed using dry nitrogen to yield a product weighing 179.4 grams and containing 7% isopropanol. The structure was confirmed by IR analysis, and the product contained 100% cationic, 58% quat and 0% amine.

EXAMPLE 5

Preparation of di-mixed C18-C22 alkyl-N-acetyl-N-[3-dimethylamino) propyl] aspartate, N'-hydrochloride salt Some 150 grams of the product of Example 2 was melted at 75° C. At this time, 10.8 grams of acetyl chloride (0.138 mole) was added dropwise over a period of ½ hour with stirring to produce a very exothermic reaction which was stirred for 2 more hours at 70° to 75° C. Some 160 grams of product was produced. The structure was confirmed by IR analysis, and the resultant product was 63% cationic.

EXAMPLE 6

Preparation of di-mixed C14-C18 alkyl-N-[3-(4-morpholino) propyl] aspartate, N'-dimethyl sulfate quaternary Some 196.1 grams (2 moles) of maleic anhydride, 1,049.6 grams (4 moles) of Alfol 1620, a mixed C14-C18 alkyl alcohol available from) ncco, 8 grams of camphor sulfonic acid and 200 milliliters of benzene were added to a reaction vessel and heated for 5 hours at 100° C. The water formed was removed during the reaction and 34.5 milliliters were removed compared to 36 milliliters theoretical. After the reaction was complete, the benzene was distilled off to yield 1,206 grams of di-mixed C14-C18 alkyl maleate having a saponification number of 175 (theoretical 180) and an acid number of 84.

Some 300 grams (0.496 mole) of the above ester was heated to 95° to 105° C while 72.6 grams (0.496 mole) of N-amino propyl morpholine was added dropwise. This mixture was then heated for 2 to 3 hours at 100° C to yield 346 grams of di-mixed C14-C18 alkyl-N-[3-(4-morpholino) propyl] aspartate.

Some 130 grams (0.174 mole) of this product was then heated with 90 milliliters isopropanol at 70° C while 21.9 grams (0.174 mole) dimethyl sulfate was added dropwise. The mixture was kept below 100° C and was stirred at 75° to 100° C for 2 hours. The solvent isopropanol was removed by bubbling nitrogen through the mixture to yield 158 grams of product, which contained 7% solvent.

EXAMPLE 7

Preparation of di-mixed C18-C22 alkyl-N-[3-(dimethylamino) propyl] methyl aspartate, N'-dimethyl sulfate quaternary Some 56.04 grams of methyl maleic anhydride (citraconic anhydride) were refluxed with 452.4 grams of Alfol 20+ in 50 milliliters benzene for ½ hour. At this point, 1.5 grams of camphor sulforic acid were added and the mixture was refluxed for 5 hours. After 9 milliliters of water were azeotroped off, the benzene was distilled off. To the reaction mixture, 51 grams N-N-dimethyl propylene diamine were added dropwise at 85° C. The reaction was slightly exothermic and the mixture was heated to 110° to 120° C for 4 hours. IR spectra of the reaction product showed disappearance of the double bond.

The reaction product was cooled to 100° C and 63 grams of dimethyl sulfate were added dropwise. This reaction is quite exothermic. The mixture was heated to 104° to 105° C for 1 hour and to 120° C for ½ hour to produce the product.

EXAMPLE 8

A series of the compounds of the present invention were evaluated as softening agents by comparing the performance on an equal actives basis with a commercially-available wash cycle fabric softener and a commercially-available rinse cycle fabric softener. The samples were prepared as 12% aqueous dispersions and those samples which were homogenized at 5500 psi and 140° C are shown in Table I with an "H" after the compound number.

The samples were rated from 0 to 7 as follows: no softening = 0, very slight softening = 1, less than standard = 2, slightly less than standard = 3, less than or equal to standard = 4, equal to standard = 5, better than or equal to standard = 6, better than standard = 7. The odor was rated: no odor = A, slight malodor = B, malodor = C.

TABLE I

| Compound | Wash Cycle Rating | Rinse Cycle Rating | Odor Rating |
| --- | --- | --- | --- |
| 1H | 1 | 5 | C |
| 2H | 1 | 5 | B |
| 3H | 2 | 5 | B |
| 4H | 0 | 5 | A |
| 5H | 2 | 5 | A |
| 6H | 1 | 4 | C |
| 7H | 1 | 6 | C |
| 8H | 1 | 6 | A |
| 9H | 0 | 4 | B |
| 10H | 1 | 4 | B |
| 11H | 1 | 5 | B |
| 12H | 0 | 4 | B |
| 13H | 0 | 5 | B |
| 14H | 2 | 6 | A |
| 15H | 0 | 7 | B |
| 16H | 0 | 6 | A |
| 17H | 3 | 6 | A |
| 18H | 1 | 6 | A |
| 19H | 5 | 5 | C |
| 20H | 5 | 5 | A |
| 21H | 1 | 5 | A |
| 21 | 5 | 5 | B |
| 22H | 4 | 5 | A |
| 22 | 3 | 5 | A |
| 23H | 4 | 3 | B |
| 24H | 1 | 4 | B |
| 25H | 5 | 5 | A |
| 26H | 3 | 0 | A |
| 27H | 0 | 5 | A |
| 28H | 3 | 0 | A |
| 29H | 1 | 3 | B |
| 30H | 1 | 5 | C |
| 31H | 1 | 1 | B |
| 32H | 0 | 5 | A |
| 33 | 2 | 2 | — |

COMPARATIVE EXAMPLE 1

The following compounds were prepared:
A. the hydrochloric acid salt of di-mixed C18-C22 alkyl-N-propyl aspartate;
B. the hydrochloric acid salt of di-mixed C18-C22 alkyl propylene diamine succinate;
C. methyl-octadecyl-N-acetyl-N-[3-(dimethylamino) propyl] aspartate-N'-hydrochloride salt; and
D. di-n-octyl-N-acetyl aspartate.

These compounds were evaluated as fabric softeners as in Example 7. The results are shown in Table II.

TABLE II

| Compound | Wash Cycle Rating | Rinse Cycle Rating | Odor Rating |
| --- | --- | --- | --- |
| A | 0 | * | A |
| B | 0 | 1 | C |
| C | 2 | 2 | C |

TABLE II-continued

| Compound | Wash Cycle Rating | Rinse Cycle Rating | Odor Rating |
|---|---|---|---|
| D | 0 | 0 | C |

*Product became too viscous and undispersable to test.

Because compound "C" had some softening, this shows that the softening ability to the compounds of the present invention is not dependant solely on the di-higher alkyl esters, while compounds "A" and "B" show that, without the tertiary amine group which can be quaternized or formed into an amine salt, softening is not obtained.

The foregoing examples are for illustration only and the compounds of the present invention shall not be deemed limited thereby but only by the following appended claims.

What is claimed is:

1. A compound having the formula

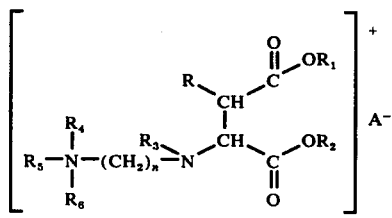

wherein:

$R$ is hydrogen or methyl;

$R_1$ and $R_2$ are the same or different and are selected from linear and branched chain alkyl groups having 8 to 22 carbon atoms;

$R_3$ is selected from formyl, and acetyl;

$R_4$ and $R_5$ are the same or different and selected from lower alkyl groups having 1 to 4 carbon atoms, and ω-hydroxyalkyl groups having 2 to 4 carbon atoms;

$R_6$ is selected from hydrogen, lower alkyl having 1 to 4 carbon atoms and benzyl;

$n$ is a whole number from 2 to 10; and

A is an anion imparting water dispersability.

2. A compound of claim 1 wherein $n$ is 2 or 3.

3. A compound of claim 1 wherein $R_1$ and $R_2$ are alkyl groups having 14 to 22 carbon atoms.

4. A compound of claim 1 wherein $R_4$ and $R_5$ are methyl, ethyl or 2-hydroxyethyl.

5. A compound of claim 1 wherein $R_6$ is hydrogen, methyl or ethyl.

6. A compound of claim 1 wherein A is methyl sulfate, ethyl sulfate, chloride, fluoride, bromide, iodide, sulfate, acetate, benzoate or gluconate.

7. A compound of claim 1 wherein
$n$ is 2 or 3;
R is hydrogen;
$R_1$ and $R_2$ are alkyl groups having 14 to 22 carbon atoms;
$R_3$ is acetyl or formyl;
$R_4$ and $R_5$ are methyl, ether, or 2-hydroxyethyl;
$R_6$ is hydrogen, methyl or ethyl; and
A is methyl sulfate, ethyl sulfate, chloride, fluoride, bromide, iodide, sulfate, acetate, benzoate or gluconate.

8. A compound of claim 7 wherein $n$ is 3.

9. The compound of claim 7 wherein $R_1$ and $R_2$ are the same and are mixed alkyl groups having 14 to 22 carbon atoms.

10. A compound of claim 7 wherein $R_4$ and $R_5$ are the same and are selected from methyl, or 2-hydroxyethyl.

11. A compound of claim 7 wherein A is formate, gluconate, methyl sulfate, ethyl sulfate or chloride.

12. A compound of claim 11 wherein A is methyl sulfate or chloride.

13. The compound of claim 1 wherein said compound is di-mixed C18-C22 alkyl-N-acetyl-N-[3-(dimethylamino) propyl] aspartate, N'-hydrochloride salt.

14. The compound of claim 1 wherein said compound is di-mixed C14-C18 alkyl-N-formyl N-[3-(dimethylamino) propyl] aspartate, N'-diethyl sulfate quaternary.

15. The compound of claim 1 wherein said compound is di-mixed C14-C18 alkyl-N-acetyl-N-[3-(dimethylamino) propyl] asparate, N'-hydrochloride salt.

16. The compound of claim 1 wherein said compound is di-mixed C14-C18 alkyl N-formyl-N-[3-(dimethylamino) propyl] asparate, N'-benzyl chloride quaternary.

* * * * *